(12) United States Patent
Kohno

(10) Patent No.: US 9,125,626 B2
(45) Date of Patent: Sep. 8, 2015

(54) LIGHT MEASUREMENT DEVICE

(75) Inventor: Satoru Kohno, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 977 days.

(21) Appl. No.: 13/144,896

(22) PCT Filed: Jan. 12, 2010

(86) PCT No.: PCT/JP2010/050206
§ 371 (c)(1),
(2), (4) Date: Jul. 15, 2011

(87) PCT Pub. No.: WO2010/087223
PCT Pub. Date: Aug. 5, 2010

(65) Prior Publication Data
US 2011/0275914 A1 Nov. 10, 2011

(30) Foreign Application Priority Data
Jan. 29, 2009 (JP) .................................. 2009-018236

(51) Int. Cl.
*A61B 5/1455* (2006.01)
*A61B 5/00* (2006.01)

(52) U.S. Cl.
CPC ............. *A61B 5/6814* (2013.01); *A61B 5/1455* (2013.01); *A61B 5/14551* (2013.01)

(58) Field of Classification Search
CPC .... A61B 5/14553; A61B 5/16; A61B 5/6814; A61B 5/02; A61B 5/021; A61B 5/024; A61B 5/08; A61B 2560/029
USPC .......................... 600/310, 322, 323, 324, 340
See application file for complete search history.

(56) References Cited

U.S. PATENT DOCUMENTS 5,016,213 A * 5/1991 Dilts et al. ...................... 600/547
5,377,100 A * 12/1994 Pope et al. ...................... 600/545

(Continued)

FOREIGN PATENT DOCUMENTS

| JP | 2000-155090 | 6/2000 |
|----|-------------|--------|
| JP | 2002-282225 | 10/2002 |

(Continued)

OTHER PUBLICATIONS

Japanese language international preliminary report on patentability dated Aug. 9, 2011 and its English language translation for corresponding PCT application PCT/JP2010/050206.

(Continued)

*Primary Examiner* — Eric Winakur
(74) *Attorney, Agent, or Firm* — Morgan, Lewis & Bockius LLP

(57) ABSTRACT

Provided is a light measurement device capable of obtaining reproducible measurement data without the necessity for bringing a subject into the state of performance of a task such as finger movement many times, the measurement data having no variation and less affected by Mayer Wave and the like caused by respiration, blood pressure, and the like other than the performance of the task. Specifically provided is a light measurement device (1) which is provided with a light transmission/reception unit controller (4) for acquiring received light amount information relating to a measurement site of the brain of a subject and a calculation unit (31) for calculating the amount of change in hemoglobin concentration, and obtains measurement data indicating the change with lapse of time in the variation amount of hemoglobin concentration during the execution of a task period in which the subject is being continuously loaded, the light measurement device being characterized by being provided with a biomonitor (60) which is disposed on the surface of the skin of the subject and detects biological information relating to the heartbeat, blood pressure, or respiration of the subject, a biomonitor control unit (32) for obtaining the biological information from the biomonitor (60), and a task period start time determination unit (35) for determining the start time of the task period on the basis of the biological information.

7 Claims, 10 Drawing Sheets

(56) References Cited

U.S. PATENT DOCUMENTS

| | | | |
|---|---|---|---|
| 5,938,531 A * | 8/1999 | Yasushi et al. | 463/36 |
| 5,983,129 A * | 11/1999 | Cowan et al. | 600/544 |
| 6,522,911 B1 | 2/2003 | Toida et al. | 600/473 |
| 7,231,240 B2 * | 6/2007 | Eda et al. | 600/322 |
| 2002/0185130 A1 | 12/2002 | Wright et al. | 128/204.21 |
| 2004/0138576 A1 | 7/2004 | Wright et al. | 600/533 |
| 2005/0171435 A1 | 8/2005 | Eda et al. | 600/475 |
| 2006/0135878 A1 | 6/2006 | Wright et al. | 600/538 |
| 2009/0112111 A1 | 4/2009 | Shimizu et al. | 600/520 |
| 2011/0082677 A1 * | 4/2011 | Kawasaki et al. | 703/11 |

FOREIGN PATENT DOCUMENTS

| | | |
|---|---|---|
| JP | 2003-102694 | 4/2003 |
| JP | 2004-522483 | 7/2004 |
| JP | 2005-198788 | 7/2005 |
| JP | 2006-026223 | 2/2006 |
| JP | 2006-109964 | 4/2006 |
| JP | 2007-044104 | 2/2007 |
| JP | 2007-111101 | 5/2007 |
| WO | WO 02/47747 A1 | 6/2002 |
| WO | WO 2007/032226 A1 | 3/2007 |
| WO | 2009/148069 * | 12/2009 |

OTHER PUBLICATIONS

Japanese language office action dated Feb. 4, 2013 and its English language translation issued in corresponding Japanese application 2010548457.

* cited by examiner

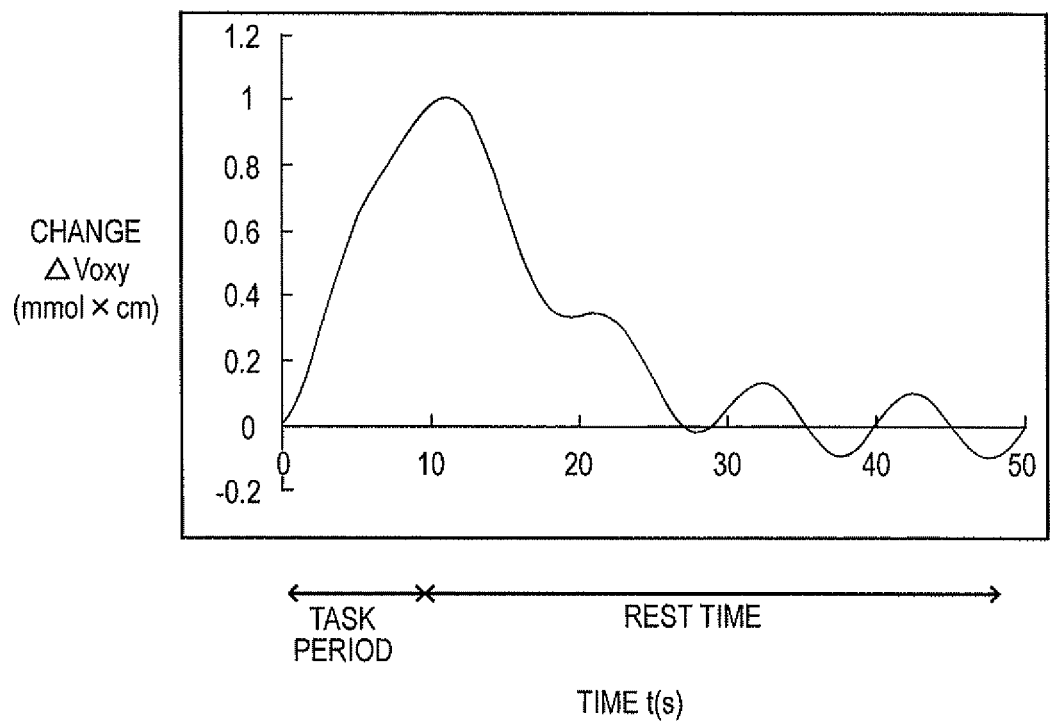

LIGHT MEASUREMENT DEVICE

TECHNICAL FIELD

The present invention relates to a light measurement device that non-invasively measures such things as change over time in blood flow and change over time in oxygen supply. In particular, the present invention relates to a light measurement device that measures change over time in blood flow or oxygen supply particularly at different sites of the brain and can be used in devices used for diagnosing disorders of the circulatory system and in oxygen monitoring devices used to diagnose whether biological tissues are normal or not.

BACKGROUND ART

Hemoglobin serves the role of carrying oxygen in blood. Because hemoglobin concentration in blood increases and decreases with vasodilation and vasoconstriction, it is known in the art that vasodilation and vasoconstriction can be detected by measuring the change $\Delta V_{hb}(t)$ in hemoglobin concentration.

A simple non-invasive method known in the art for obtaining biological measurements uses a light detection controller and the fact that the change $\Delta V_{hb}(t)$ in hemoglobin concentration corresponds to the oxygen metabolism function in a tested subject's body. The change $\Delta V_{hb}(t)$ in hemoglobin concentration can be determined by irradiating the tested subject with light whose wavelength varies from visible light to the near-infrared range and measuring the change (received light amount information) in intensity of light that passes through the body.

Hemoglobin bonds with oxygen to become oxyhemoglobin and dissociates from oxygen to become deoxyhemoglobin. It is known that, in the brain, the sites that are activated by blood flow redistribution are supplied with oxygen and that the concentration of oxyhemoglobin created by the bonding with oxygen increases. Hence, the change $\Delta V_{oxy}$ in oxyhemoglobin concentration can be measured and used to observe brain activity. Because the absorption spectrum in the visible light to near-infrared spectrum is different between oxyhemoglobin and deoxyhemoglobin, near-infrared light of differing wavelengths (e.g., 780 nm, 805 nm, 830 nm) can be used to determine the change $\Delta V_{oxy}(t)$ in oxyhemoglobin concentration and the change $\Delta V_{deoxy}(t)$ in deoxyhemoglobin concentration.

This has led to the development of light measurement devices equipped with light transmission probes and light reception probes that are used for the non-invasive measurement of brain activities. With the light measurement device, near-infrared light is emitted into the brain from the light transmission probes that are positioned on the surface of the tested subject's scalp, and the change in intensity of the near-infrared light that emerges from the brain is detected as the received light amount information by light reception probes that are also positioned on the scalp surface. The near-infrared light passes through the scalp tissue, bone tissue and the like and is absorbed by the oxyhemoglobin or deoxyhemoglobin in the blood. Hence, such light measurement device equipped with light transmission probes and light reception probes and employing near-infrared light of three different wavelengths can be used to obtain from the received light amount information such measurement data as change $\Delta V_{oxy}(t)$ in oxyhemoglobin concentration, change $\Delta V_{deoxy}(t)$ in deoxyhemoglobin concentration and, by further calculations based on them, change $\Delta V_{hb}(t)$ in hemoglobin concentration over time at the brain's measured sites.

Furthermore, light measurement devices have been developed which measure data such as change $\Delta V_{oxy}(t)$ in oxyhemoglobin concentration over time at a plurality of brain measurement sites associated with brain functions such as movement, sensory perception and thinking and are used in the medical field for such purposes as the diagnosis of brain functions and circulatory system disorders. An example of an art that is used in such light measurement devices is near-infrared spectroscopy ("NIRS"). (See, for example, Patent Literature 1.)

With a NIRS, a holder is used so that a plurality of light transmission probes and a plurality of light reception probes are closely attached to the surface of the scalp of the tested subject in a predetermined array. The holder may be shaped like a bowl to fit the shape of the scalp surface. The holder has a plurality of penetrating holes formed therein with a light transmission probe or a light reception probe being inserted into a penetrating hole. This maintains a certain distance ("channel dimension") between the light transmission probes and the light reception probes and allows received light amount information to be obtained from sites that are located at a specific depth below the scalp surface.

FIG. 2 is a plan view showing one example of the positional relationship among nine light transmission probes and eight light reception probes in a light transmission/reception unit in a NIRS such as the afore-described. The light transmission probes 12 and the light reception probes 13 are positioned so that they alternate with each other in both an oblique direction and a direction orthogonal to the oblique direction.

Even though the light that is emitted from a light transmission probe 12 is received not only by adjacent light reception probes 13 but also by light reception probes 13 that are more distantly located, for the sake of simplicity of the explanation here, it is assumed that the light is detected only by adjacent light reception probes 13. One of the nine light transmission probes 12 is selected and light is emitted from it. This is sequentially repeated so that a total of 24 received light amount information is obtained from channel numbers #1, through #24 shown in FIG. 2.

Measurement data (change $\Delta V_{oxy}(t)$ in oxyhemoglobin concentration over time, etc.) that is derived from the received light amount information obtained by NIRS is displayed as images on a monitor screen so that they can be observed by physicians, medical technicians and the like.

One biological measurement method that can be used to diagnose whether or not a biological tissue is normal involves physicians, medical technicians or the like providing a stimulus (referred to as "load" or "task") to the tested subject and observing the measurement data that is obtained as the brain of the tested subject is activated. FIG. 4 shows one example of a measurement data showing the change $\Delta V_{oxy}(t)$ in oxyhemoglobin concentration over time at a particular measurement site (e.g., channel number #1). In the measurement data, the vertical axis plots the change $\Delta V_{oxy}$ in oxyhemoglobin concentration in comparison to the initial oxyhemoglobin concentration at the time the NIRS system was worn by the tested subject, and the horizontal axis plots time t.

One example of a biological measurement method such as this involves a physician, medical technician or the like keeping track of time while the tested subject is made to perform the task of moving a finger (finger-tapping) for a set amount of time Y ("task period"). This is followed by a resting period for a set amount of time X ("rest period") to return to a steady-state. The tested subject is then again made to perform the task of moving the finger for a set amount of time Y which is then followed by resting for a set amount of time X to return to a steady-state. This alternating cycle of the task period followed by the rest period is repeated R times ("task repetition count"). This creates measurement data such as that shown in FIG. 4 depicting the change $\Delta V_{oxy}$ (t) in oxyhemoglobin concentration over time that repeats R times.

There are light measurement devices wherein, prior to starting a measurement, a physician, medical technician or the like uses an input screen that is displayed on a monitor screen to input and set measurement conditions such as time Y that defines the task period, time X that defines the rest period and the task repetition count R. FIG. 5 shows one example of an input screen that is used for setting the measurement conditions in a previous light measurement device. A keyboard or the like is used to enter the measurement conditions from the input screen. The measurement conditions may be a task period Y of 10 seconds, rest period X of 40 seconds and a task repetition count R of 5. When the measurement is performed, the light measurement device uses the measurement conditions that are entered to display images that provide instructions to transition from a task period to a rest period when that is required and to transition from a rest period to a task period when that is required. The physician, a medical technician or the like observes the images that are displayed on the monitor screen and issues instructions to the test subject who follows the instructions from the physician, medical technician or the like and alternates between a rest period and a task period for a plurality of times, R.

FIG. 6 shows the theoretical measurement data that should be obtained when a test subject is made to perform the task of moving the finger for a set time Y. The theoretical measurement data is characterized by change over time that increases with a substantially constant slope. However, the actual change $\Delta V_{oxy}$ (t) in oxyhemoglobin concentration over time that is generated will be as shown in FIG. 4.

This is because, with a human brain, Mayer Wave variations in arterial pressure occur due to factors such as respiration and blood pressure, regardless of whether the finger moving task is being performed or not. FIG. 7 shows one example of a graph (biological information) showing the change $\Delta V_{oxy}$ (t) in oxyhemoglobin concentration over time due to Mayer Waves. As FIG. 7 shows, the period of the Mayer Waves is approximately 10 seconds. However, the Mayer Wave period fluctuates slightly even in the same person and can be, for example, 8 seconds at times and 12 seconds at another.

This means that the measurement data that shows the actual change $\Delta V_{oxy}$ (t) in oxyhemoglobin concentration over time such as that shown in FIG. 4 is a superimposition of the theoretical change $\Delta V_{oxy}$ (t) in oxyhemoglobin concentration such as that shown in FIG. 6 and the change $\Delta V_{oxy}$ (t) in oxyhemoglobin concentration caused by Mayer Wave such as that shown in FIG. 7.

Even though the period of the Mayer Wave is approximately 10 seconds, it is unknown, when the finger movement task is started, as to whether the amount of change $\Delta V_{oxy}$ (t) in oxyhemoglobin concentration caused by Mayer Waves is 0.00 mM×cm or 0.10 mM×cm. If the change $\Delta V_{oxy}$ (t) in oxyhemoglobin concentration due to Mayer Wave is as shown in FIG. 7, the resulting measurement data becomes as shown in FIG. 4. However, if the Mayer Wave is out of phase by 90° as compared to what is shown in FIG. 7, the resulting measurement data will be as shown in FIG. 9 where the theoretical change $\Delta V_{oxy}$ (t) in oxyhemoglobin concentration over time such as that shown in FIG. 6 is superimposed with the change $\Delta V_{oxy}$ (t) in oxyhemoglobin concentration over time due to Mayer Wave such as that shown in FIG. 8. Also, if the Mayer Wave is out of phase by 180° as compared to what is shown in FIG. 7, the resulting measurement data will be as shown in FIG. 11 where the theoretical change $\Delta V_{oxy}$ (t) inoxyhemoglobin concentration over time such as that shown in FIG. 6 is superimposed with the change $\Delta V_{oxy}$ (t) in oxyhemoglobin concentration over time due to Mayer Wave such as that shown in FIG. 10. If the Mayer Wave is out of phase by 270° as compared to what is shown in FIG. 7, the resulting measurement data will be as shown in FIG. 13 where the theoretical change $\Delta V_{oxy}$ (t) inoxyhemoglobin concentration over time such as that shown in FIG. 6 is superimposed with the change $\Delta V_{oxy}$ (t) in oxyhemoglobin concentration over time due to Mayer Wave such as that shown in FIG. 12.

In other words, when a test subject is made to perform the finger movement task for a set amount of time Y, the measurement data that is obtained may be the measurement data shown in FIG. 4, the measurement data shown in FIG. 9, the measurement data shown in FIG. 11 or the measurement data shown in FIG. 13. The respective measurement data look significantly different from each other as shown in FIG. 14.

It is said that certain mental disorders are characterized by a typical rise (slope) in the change $\Delta V_{oxy}$ (t) in oxyhemoglobin concentration. However, it would be difficult for a physician, medical technician or the like to evaluate whether a subject is suffering from depression just by observing measurement data that is affected by variations caused by Mayer Wave. For this reason, with previous biological measurement methods, the tested subject is made to repeat a task for R times during the task period. The resulting R pieces of measurement data that is obtained are added and averaged to reduce the effects of the Mayer Wave, and measurement data that is free of variability is displayed on the monitor screen.

PRIOR ART LITERATURE

Patent Literature

Patent Literature 1: JP 2006-109964 A

OVERVIEW OF THE INVENTION

Problems to be Solved by the Invention

However, with previous biological measurement methods, displaying measurement data on a monitor screen free of variability and having reduced effects of Mayer Wave required having the test subject repeat the task R times during a task period. This means that the tested subject has to wear the light transmission/reception unit 11 for an extended period, creating an unavoidable problem of discomfort. There also is research under way that involves measuring brain activity as a part of research on the use of brain-machine interface as a man-machine (external device) interface. However, with the previous biological measurement methods, it is not possible to control the machine in real time (in one task period).

Hence, it is the object of the present invention to provide a light measurement device that can generate measurement data with good reproducibility, free of variability and having reduced effects of variations arising from non-task related factors such as the Mayer Wave caused by respiration, blood pressure and the like and without requiring the tested subject to repeatedly perform a task such as finger movement.

Means for Solving the Problems

To solve the afore-described problems, the present invention is a light measurement device for obtaining measurement data that shows change over time in hemoglobin concentration while a tested subject is performing a load during a task period, the light measurement device including: a light transmission/reception unit including light transmission probes that are positioned on the surface of a scalp of the tested subject and light reception probes that are positioned on the surface of the scalp; a light transmission/reception unit controller for obtaining received light amount information regarding measurement sites of a brain of the tested subject by controlling so that the light transmission probes emit light to the scalp surface and the light reception probes detect light that emerges from the scalp surface; a calculation unit for calculating the change in hemoglobin concentration based on the received light amount information; a biomonitor that is positioned on the skin surface of the tested subject for detecting biological information related to the heart rate, blood pressure or respiration of the tested subject; a biomonitor controller for obtaining biological information from the biomonitor; and a task period start time determination unit for determining a starting time for the task period based on the biological information.

Here, the term "load" refers not only to an activity that entails some motion by the tested subject such as moving a finger (finger-tapping) or writing something but also to activities that are passive for the tested subject but still elicits a brain activity such as having the tested subject listen to some sound or to look at some images.

With the light measurement device according to the present invention, a biomonitor is positioned on the skin surface of the tested subject simply by placing the light transmission/reception unit on the surface of the tested subject's scalp. A biomonitor controller extracts biological information on the tested subject from the biomonitor such as heart rate, blood pressure, respiration and the like. A task period start time determination unit decides the starting time for the task period based on biological information. For example, if a biological information indicative of Mayer Wave caused by respiration, blood pressure and the like shows that the amount of change $\Delta V_{oxy}$ (t) in oxyhemoglobin concentration caused by Mayer Wave is 0.00 mM×cm and that it is rising, an image is displayed on the monitor screen that instructs the tested subject to transition to a task period where the subject's finger is moved. The physician, medical technician or the like who is observing the images displayed on the monitor screen issues the instruction to the tested subject who, in accordance with the instruction from the physician, medical technician or the like, initiates the task period using, as the starting timing, the point in time when the amount of change $\Delta V_{oxy}$ (t) in oxyhemoglobin concentration caused by Mayer Wave is 0.00 mM×cm and rising. The resulting measurement data that is obtained will not be superimposed with the change $\Delta V_{oxy}$ (t) in oxyhemoglobin concentration caused by Mayer Wave shown in FIG. 8, or with the change $\Delta V_{oxy}$ (t) in oxyhemoglobin concentration caused by Mayer Wave shown in FIG. 10, or with the change $\Delta V_{oxy}$ (t) in oxyhemoglobin concentration caused by Mayer Wave shown in FIG. 12 but will always be superimposed with the change $\Delta V_{oxy}$ (t) in oxyhemoglobin concentration over time caused by Mayer Wave shown in FIG. 7.

Effects of the Invention

As afore-described, with a light measurement device according to the present invention, there is no need for a tested subject to repeatedly perform a task such as moving a finger, and measurement data with reproducibility and free of variability and with reduced effects of Mayer Wave caused by respiration, blood pressure and the like is produced.

Other Means for Solving the Problems, and Effects

With the light measurement device according to the present invention, the task period start time determination unit can be made to display an image that instructs to transition to a task period. Also, with the light measurement device according to the present invention, the task period start time determination unit can be made to initiate the imposition of a load on the tested subject.

The present invention is a light measurement device for obtaining measurement data that shows change over time in hemoglobin concentration while a tested subject is performing a load during a task period, the light measurement device including: a light transmission/reception unit including light transmission probes that are positioned on the surface of a scalp of the tested subject and light reception probes that are positioned on the surface of the scalp; a light transmission/reception unit controller for obtaining received light amount information regarding measurement sites of a brain of the tested subject by controlling so that the light transmission probes emit light to the scalp surface and the light reception probes detect light that emerges from the scalp surface; a calculation unit for calculating the change in hemoglobin concentration based on the received light amount information; a biomonitor that is positioned on the skin surface of the tested subject for detecting biological information related to heart rate, blood pressure or respiration of the tested subject; a biomonitor controller for obtaining biological information from the biomonitor; and an emission start time decision unit for determining the emission starting time for emitting light from the light transmission probe to a scalp surface based on the biological information.

With the light measurement device according to the present invention, not only is the light transmission/reception unit positioned on the surface of the tested subject's scalp but the biomonitor is also positioned on the surface of the tested subject's skin. The biomonitor controller obtains biological information such as the tested subject's heart rate, blood pressure and respiration from the biomonitor. The emission start time decision unit uses these biological information as the basis for determining the emission starting time for emitting light to the scalp surface from the light transmission probe. For example, if the biological information that shows Mayer Wave caused by respiration, blood pressure or the like indicates that the amount of change $\Delta V_{oxy}$ (t) in oxyhemoglobin concentration caused by Mayer Wave has become 0.00 mM×cm and is rising, light is emitted from the light transmission probe to the scalp surface. In other words, the emission starting time occurs always when the amount of change $\Delta V_{oxy}$ (t) in oxyhemoglobin concentration caused by Mayer Wave has become 0.00 mM×cm and is rising. The result is the generation of measurement data that is reproducible, free of variability and with lessened effects of Mayer Wave and the like caused by respiration, blood pressure and the like.

Furthermore, since reproducible measurement data is obtained, if a brain-machine interface is used to control some apparatus when the amount of change $\Delta V_{oxy}$ (t) in oxyhemoglobin concentration exceeds a certain peak value (threshold value), the apparatus can be controlled with precision.

Furthermore, with the light measurement device according to the present invention, the biomonitor for obtaining biological information about a tested subject's respiration may be an elastic belt or a respiration monitoring device that is worn around the tested subject's abdomen or chest.

Furthermore, with the light measurement device according to the present invention, the biomonitor for obtaining biological information about a tested subject's blood pressure may be a pressure sensor device that is attached to the tested subject or an electrocardiogram monitor that uses electrodes that are attached to the tested subject's chest, arms or legs.

Furthermore, with the light measurement device according to the present invention, the biomonitor for obtaining biological information about a tested subject's heart rate may be an accelerometer that is attached to the tested subject.

BRIEF DESCRIPTION OF THE FIGURES

FIG. 4 shows one example of a measurement data showing the change $\Delta V_{oxy}$ (t) over time in oxyhemoglobin concentration.

FIG. 5 shows one example of an input screen that is used for setting the measurement conditions in a previous light measurement device.

EMBODIMENTS OF THE INVENTION

Embodiments of the present invention are described next with reference to figures. The present invention is not limited to the following embodiments, and needless to say, various variations are possible without deviating from the gist of the present invention.

Embodiment 1

Figure 1:
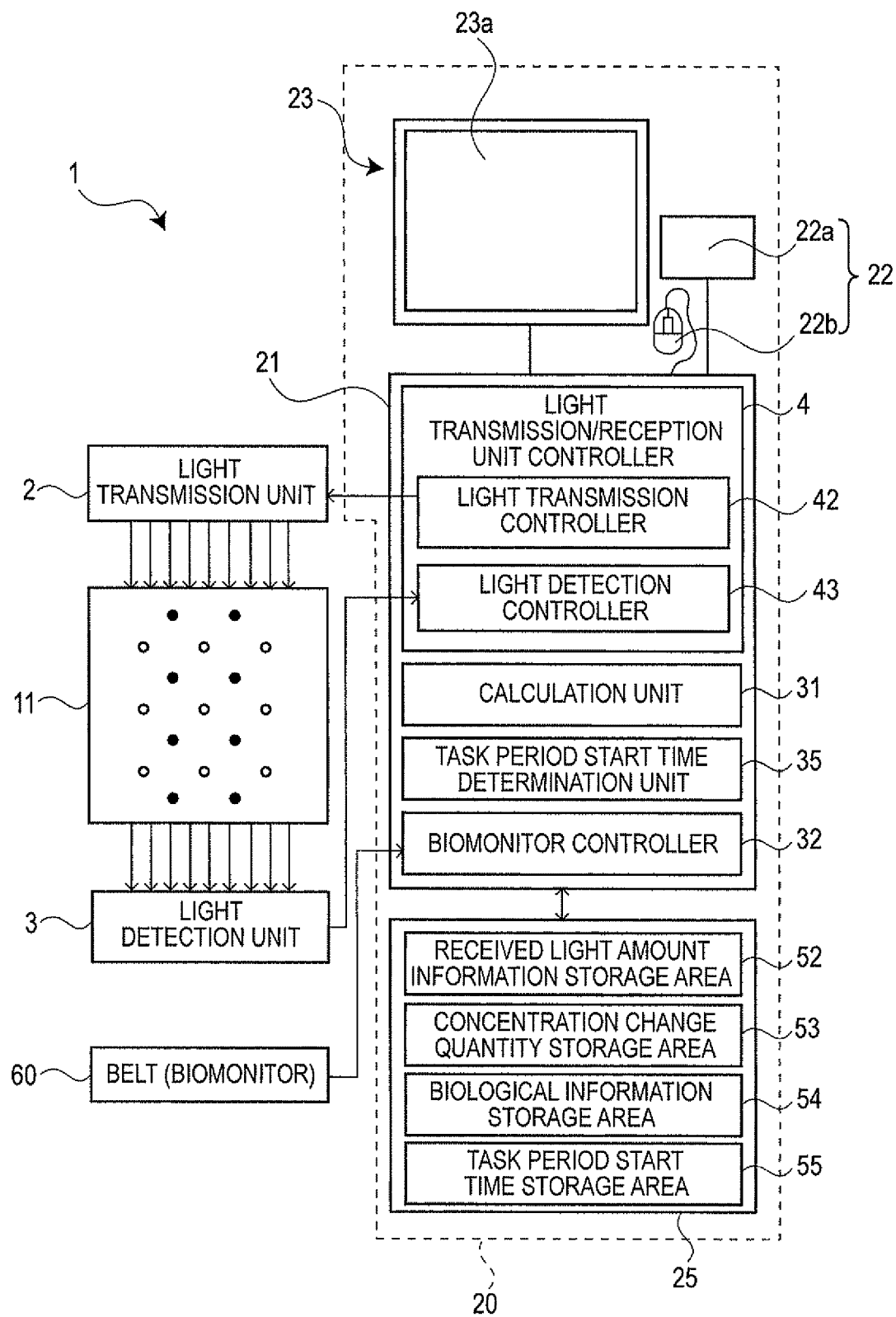
FIG. 1 is a block diagram showing the configuration of one embodiment of a light measurement device according to the present invention.

FIG. 1 is a block diagram showing the configuration one embodiment of a light measurement device according to the present invention. The light measurement device 1 includes a light transmission/reception unit 11 that is placed on the surface of the tested subject's scalp; a light transmission unit 2; a light detection unit 3; an elastic belt (biomonitor) 60 that is worn around the tested subject's abdomen; and a controller (computer) 20 that controls the overall light measurement device 1.

Figure 2:
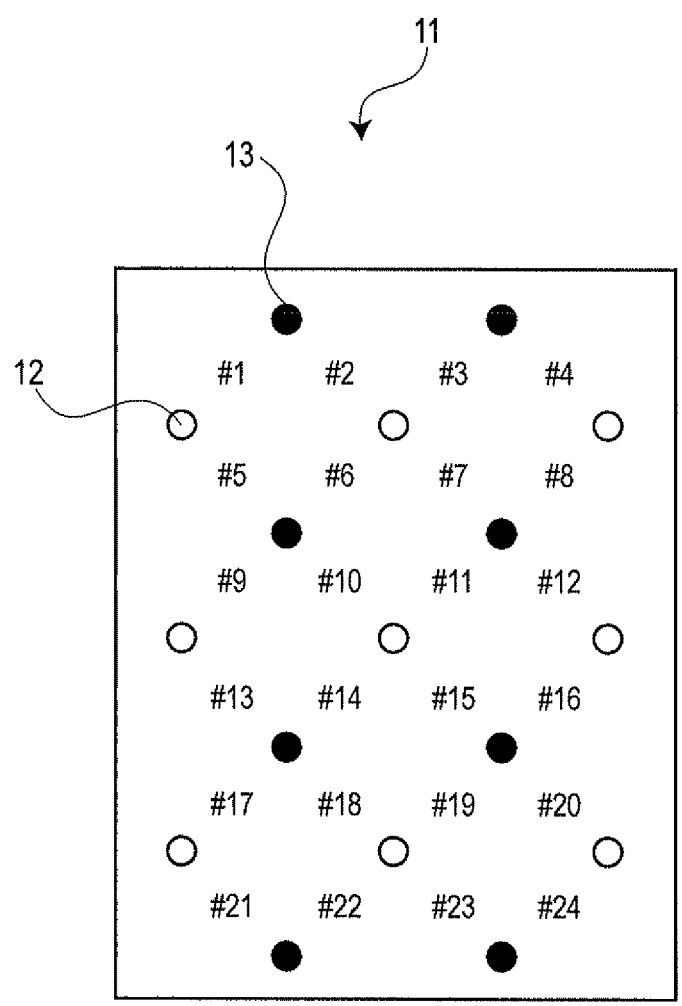
FIG. 2 is a plan view showing the positional relationship among nine light transmission probes and eight light reception probes in a NIRS.

FIG. 2 is a plan view showing the positional relationship of nine light transmission probes 12 and eight light reception probes 13 in the light transmission/reception unit 11.

The "load" that is imposed on the tested subject when using the light measurement device 1 is a verbal fluency task (VFT) which is used in clinical work and research in psychology as one test of the frontal lobe function. The verbal fluency task is a task where the tested subject is required to list as many words and the like that meet certain conditions within a specific amount of time Y (e.g., 10 seconds). For example, the instruction may be to write as many nouns as possible that start with the Japanese character "あ" ("a"). The tested subject has to write words such as "あめんぼう" ("amenbo"), "あめ" ("ante"), etc. When the tested subject is instructed to write as many nouns as possible that start with the Japanese character "い" ("i"), the tested subject has to write "いぬ" ("inu"), "いえ" ("ie"), etc. The physicians, medical technicians and the like then monitor the change $\Delta V_{oxy}$ (t) in oxyhemoglobin concentration over time during the task period that the tested subject is requested to perform the verbal fluency task and evaluate the rising edge (slope) of the change $\Delta V_{oxy}$ (t) in oxyhemoglobin concentration which is said to characterize certain mental disorders.

As FIG. 2 shows, the light transmission/reception unit 11 includes nine light transmission probes 12 and eight light reception probes 13. The light transmission probes 12 and light reception probes 13 are alternately positioned on the surface of the tested subject's scalp to be in a direction oblique to each other and in a direction orthogonal to the oblique direction. The distance between the light transmission probes 12 and light reception probes 13 is 30 mm. The nine light transmission probes 12 emit light, and the eight light reception probes 13 detect light intensity.

The light transmission unit 2 sends light to one of the light transmission probes 12 among the nine light transmission probes 12 that is selected by a drive signal that is input to the light transmission unit 2 from a computer 20. For example, light of three different wavelengths of 780 nm, 805 nm and 830 nm is used as the light, and the light of 3 different wavelengths is sequentially emitted.

The near-infrared light that is individually received by the eight light reception probes 13 is individually detected by the light detection unit 3, and the eight light reception probes output eight different received light amount information to the computer 20. In other words, when light of 3 different wavelengths is sent to one light transmission probe 12, this results in 24 (i.e., 3 wavelengths×8, the number of light reception probes 12) received light amount information $\Delta A_{780}$ (t), $\Delta A_{805}$ (t), $\Delta A_{830}$ (t) to be output to the computer 20.

The belt (biomonitor) 60 is worn around the tested subject's abdomen, and its contraction is used to detect biological information W(t) that arises from respiration. Specifically, when the tested subject inhales air, the belt 60 expands, and biological information W(t) with a large numerical value that indicates inhalation of air is detected. On the other hand, when the tested subject exhales air, the belt 60 contracts, and biological information W(t) with a small numerical value that indicates exhalation of air is detected. This means that the biological information W(t) repeatedly alternates between a large numerical value and a small numerical value just like the Mayer Wave. The period of the biological information W(t) caused by respiration is approximately 10 seconds. Just like the Mayer Wave, the period of the biological information W(t) can vary somewhat even in the same individual and may be, for example, 8 seconds at times and 12 seconds at others. The belt 60 outputs the detected biological information W(t) to the computer 20.

The computer 20 is equipped with a CPU 21, a memory (storage unit) 25, a display device 23 such as a monitor screen 23a, and an input device 22 such as a keyboard 22a or mouse 22b.

The processes performed by CPU 21 can be divided into the following functional blocks: a light transmission/reception unit controller 4 which controls the light transmission unit 2 and the light detection unit 3; a calculation unit 31 which calculates change $\Delta V_{oxy}(t)$ in oxyhemoglobin concentration; a biomonitor controller 32 which obtains biological information W(t) related to respiration; and a task period start time determination unit 35 which determines the starting time $t_a$ of a task period.

Furthermore, the memory 25 includes: a received light amount information storage area 52 where received light amount information $\Delta A_{780}(t)$, $\Delta A_{805}(t)$ and $\Delta A_{830}(t)$ is stored; a concentration change quantity storage area 53 where the change $\Delta V_{oxy}(t)$ in oxyhemoglobin concentration is stored; a biological information storage area 54 where biological information W(t) is stored; and a task period start time storage area 55 where the starting time $t_a$ of the task period is stored.

Based on the received light amount information $\Delta A_{780}(t)$, $\Delta A_{805}(t)$ and $\Delta A_{830}(t)$ and using the following publicly known mathematical equations (1), (2) and (3), the change $\Delta V_{oxy}(t)$ in oxyhemoglobin concentration, the change $\Delta V_{deoxy}(t)$ in deoxyhemoglobin concentration and the change $\Delta V_{hb}(t)$ in hemoglobin concentration can be calculated. However, to simplify the explanation here, the explanation here is limited only to monitoring the change $\Delta V_{oxy}(t)$ in oxyhemoglobin concentration.

$$\Delta V_{oxy}(t) = -1.48847 \Delta A_{780}(t) + 0.5970 \Delta A_{805}(t) + 1.4847 \Delta A_{830}(t) \quad (1)$$

$$\Delta V_{deoxy}(t) = 1.8545 \Delta A_{780}(t) - 0.2394 \Delta A_{830}(t) \quad (2)$$

$$\Delta V_{hb}(t) = \Delta V_{oxy}(t) + \Delta V_{deoxy}(t) 1.6 \Delta A_{780}(t) \quad (3)$$

The light transmission/reception unit controller 4 includes: a light transmission controller 42 that outputs drive signals to the light transmission unit 2; and a light detection controller 43 which receives received light amount information $\Delta A_{780}(t)$, $\Delta A_{805}(t)$ and $\Delta A_{830}(t)$ from the light detection unit 3 and stores the received light amount information $\Delta A_{780}(t)$, $\Delta A_{805}(t)$ and $\Delta A_{830}(t)$ in the received light amount information storage area 52.

The light transmission controller 42 controls the output of the drive signal to the light transmission unit 2 which causes light to be sent to the light transmission probes 12. For example, the light transmission controller 42 outputs a drive signal to the light transmission unit 2 which causes light to be sequentially sent to nine light transmission probes 12 in, for example, the following manner: a 780 nm light is first sent to a first light transmission probe 12 for 0.15 seconds, followed by a 805 nm light for 0.15 seconds and then a 830 nm light for 0.15 seconds, which is followed by a 780 nm light to be sent to a second light transmission probe 12 for 0.15 seconds, followed by a 805 nm light for 0.15 seconds and then a 830 nm light for 0.15 seconds. When the light transmission unit 2 has completed sending light to the ninth light transmission probe 12, the light transmission controller 42 again outputs a drive signal to the light transmission unit 2.

Whenever light is emitted from one light transmission probe 12, the light detection controller 43 receives received light amount information $\Delta A_{780}(t)$, $\Delta A_{805}(t)$ and $\Delta A_{830}(t)$ from the light detection unit 3 and stores the 24 pieces of received light amount information $\Delta A_{780}(t)$, $\Delta A_{805}(t)$ and $\Delta A_{830}(t)$ detected by the eight light reception probe 13 in the received light amount information storage area 52. This means that if light is emitted from nine light transmission probes 12, 216 pieces of received light amount information $\Delta A_{780}(t)$, $\Delta A_{805}(t)$ and $\Delta A_{830}(t)$ are stored in the received light amount information storage area 52.

The calculation unit 31 performs a control so that the received light amount information $\Delta A_{780}(t)$, $\Delta A_{805}(t)$ and $\Delta A_{830}(t)$ that are stored in the received light amount information storage area 52 are used to obtain the received light amount information $\Delta A_{780}(t)$, $\Delta A_{805}(t)$ and $\Delta A_{830}(t)$ for the light that is emitted by light transmission probe 12 and received by light reception probes 13 that are adjacent to the light transmission probe 12. The received light amount information $\Delta A_{780}(t)$, $\Delta A_{805}(t)$, $\Delta A_{830}(t)$ that are obtained are used with the aforesaid equations (1), (2) and (3) to calculate the change $\Delta V_{oxy}(t)$ in oxyhemoglobin concentration which is then stored in the concentration change quantity storage area 53.

The biomonitor controller 32 performs a control so that biological information W(t) from belt 60 is received for a set time interval $\Delta T_1$ (e.g., 0.1 seconds) and is stored in the biological information storage area 54.

It is assumed here that the numerical value of the biological information W(t) that arises from respiration cyclically varies between $+W_a$ representing a large numerical value and $-W_a$ representing a small numerical value with a period of approximately 10 seconds.

The task period start time determination unit 35 uses the biological information W(t) to perform a control that decides the starting time $t_a$ of the task period, displays an image that instructs to commence the task period at starting time $t_a$, stores starting time $t_a$ in the task period start time storage area 55, and displays an image that instructs to end the task period when task time Y has elapsed from the starting time $t_a$.

Specifically, the task period start time determination unit 35 determines the starting time $t_a$ of a task period by detecting when the biological information W(t) has exceeded a reference threshold value ($-W_a \times 0.1$) after once decreasing to a lower threshold value ($-W_a \times 0.9$) and then allowing a set time $\Delta T_2$ (e.g., 100 milliseconds) to elapse after the said detection and displays an image on the monitor screen 23a that instructs to commence the starting time $t_a$ for the task period. The starting time $t_a$ is also stored in the task period start time storage area 55. Thereafter, after the elapse of the task time Y (e.g., 10 seconds) from the starting time $t_a$, an image is displayed on the monitor screen 23a that instructs the end of the task period.

This means that, because the light measurement device 1 always defines the starting time $t_a$ of a task period to be when a set time $\Delta T_2$ (e.g., 100 milliseconds) has elapsed after the detection of the biological information W(t) that exceeds a reference threshold value ($-W_a \times 0.1$) after once decreasing to the lower threshold value ($-W_a \times 0.9$), the effect of biological information W(t) caused by respiration is reduced, and measurement data that is reproducible and free of variability is obtained.

When observing the measurement data that is obtained by the light measurement device 1, physicians, medical technicians and the like observe and evaluate the rising pattern of the change $\Delta V_{oxy}$ (0 in oxyhemoglobin concentration, aware in advance that biological information W(t) having a certain waveform caused by respiration is superimposed on the observed change $\Delta V_{oxy}$ (t) in oxyhemoglobin concentration. The respiration causes change $\Delta V_{oxy}$ (t) over time in oxyhemoglobin concentration of a certain waveform.

Figure 3:
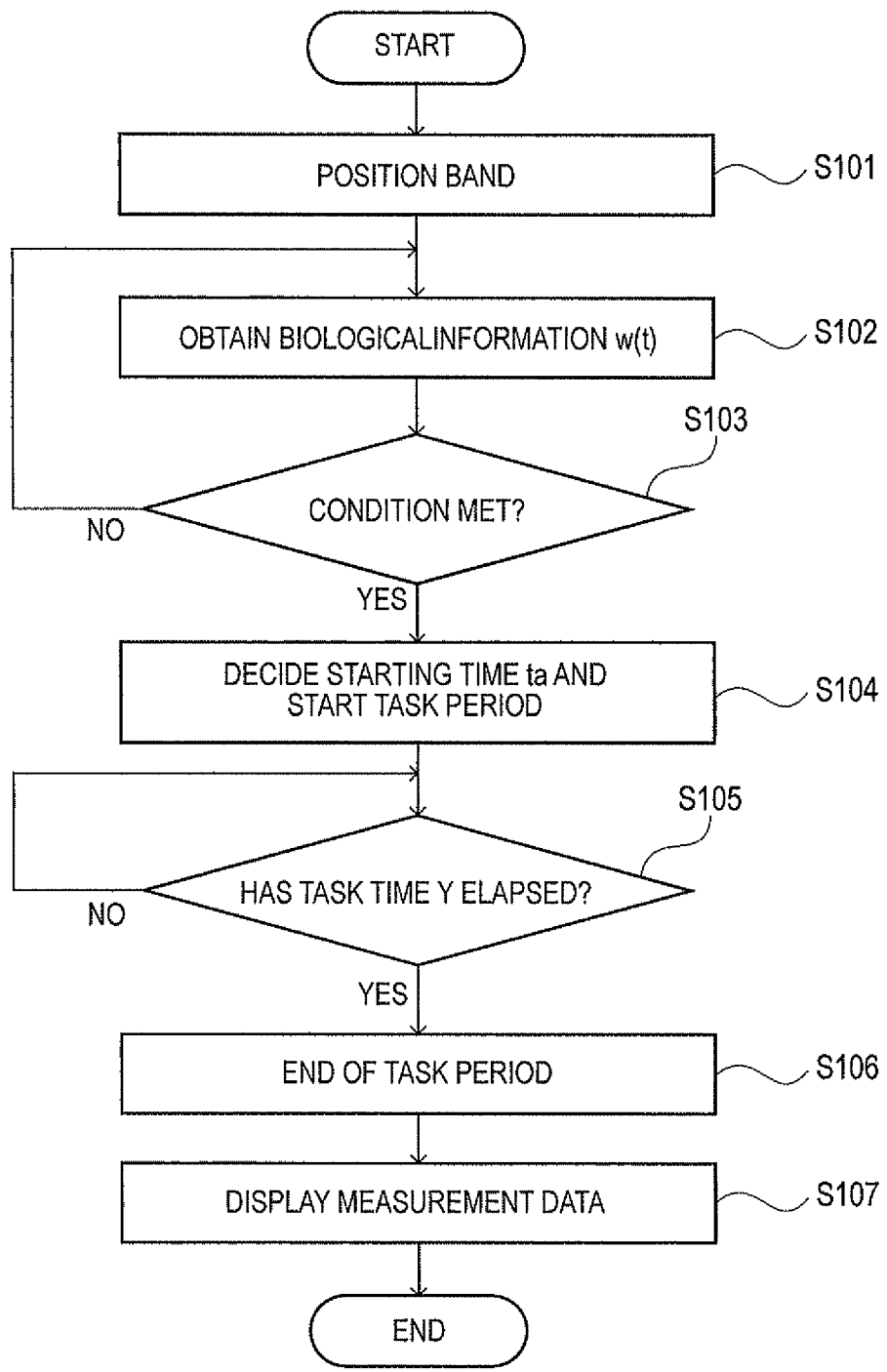
FIG. 3 is a flowchart used for explaining one example of a measurement method performed by the light measurement device.
Figure 6:
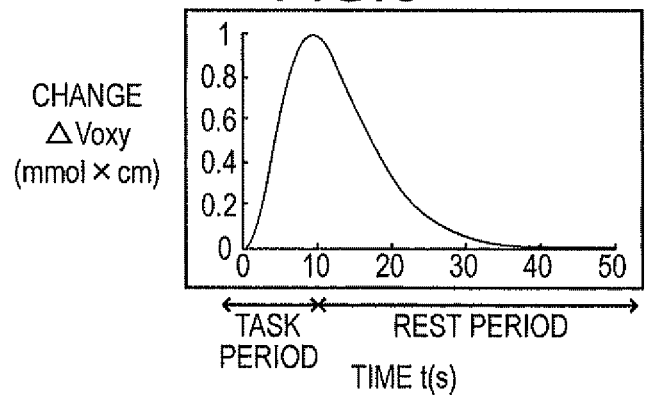
FIG. 6 is a measurement data showing the theoretical change $\Delta V_{oxy}$ (t) over time in oxyhemoglobin concentration.
Figure 7:
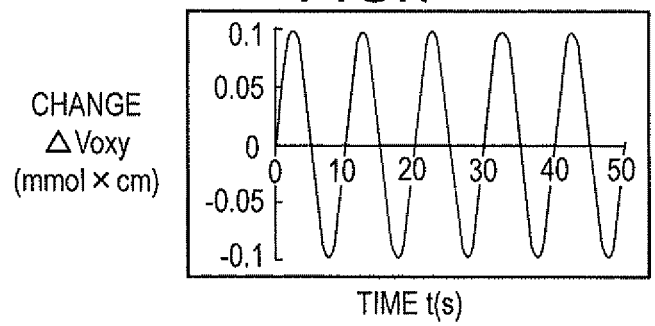
FIG. 7 shows one example of a graph showing the change $\Delta V_{oxy}$ (t) over time in oxyhemoglobin concentration caused by Mayer Wave.
Figure 8:
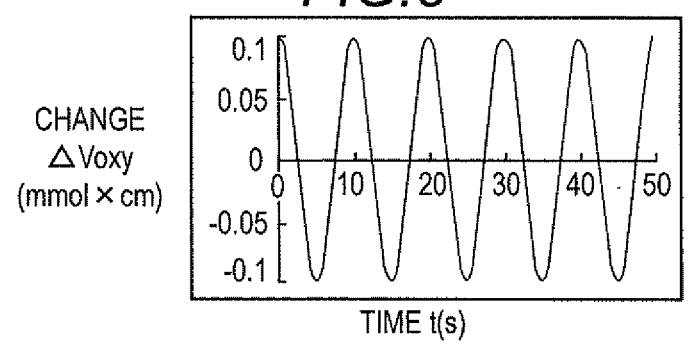
FIG. 8 shows another example of a graph showing the change $\Delta V_{oxy}$ (t) over time in oxyhemoglobin concentration caused by Mayer Wave.
Figure 9:
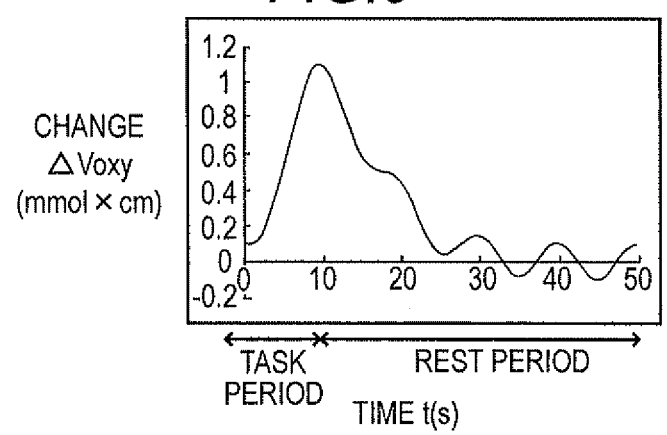
FIG. 9 shows another example of a measurement data showing the change $\Delta V_{oxy}$ (t) over time in oxyhemoglobin concentration.
Figure 10:
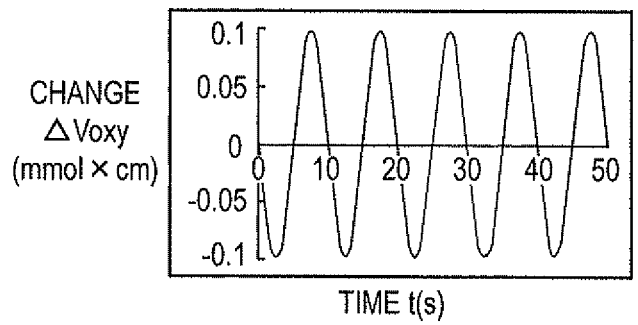
FIG. 10 shows another example of a graph showing the change $\Delta V_{oxy}$ (t) over time in oxyhemoglobin concentration caused by Mayer Wave.
Figure 11:
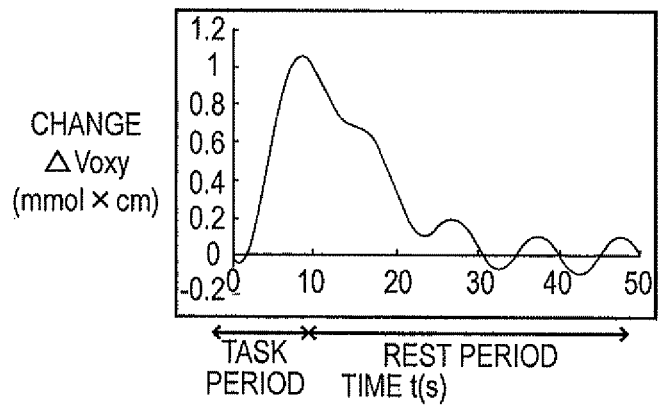
FIG. 11 shows another example of a measurement data showing the change $\Delta V_{oxy}$ (t) over time in oxyhemoglobin concentration.
Figure 12:
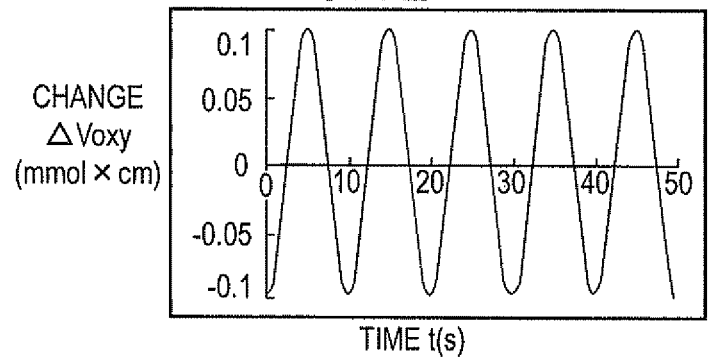
FIG. 12 shows another example of a graph showing the change $\Delta V_{oxy}$ (t) over time in oxyhemoglobin concentration caused by Mayer Wave.
Figure 13:
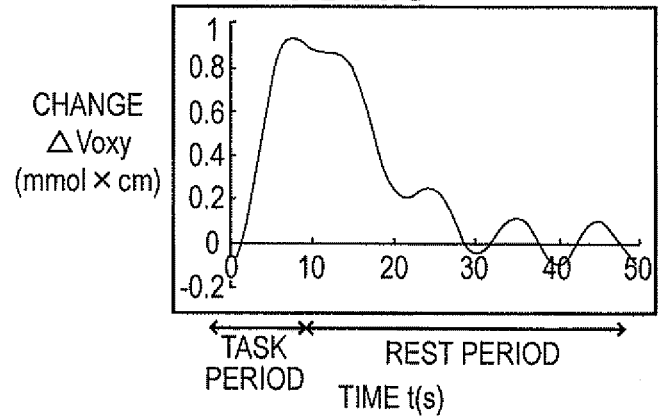
FIG. 13 shows another example of a measurement data showing the change $\Delta V_{oxy}$ (t) over time in oxyhemoglobin concentration.
Figure 14:
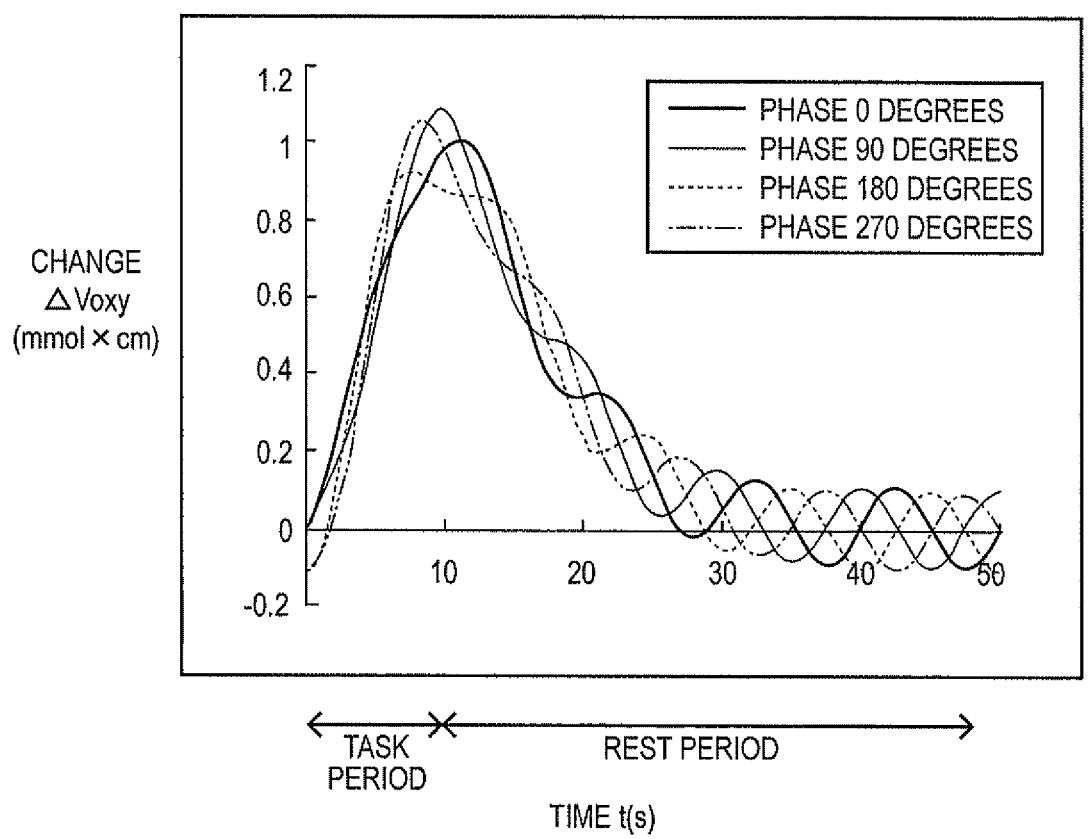
FIG. 14 shows measurement data showing the change $\Delta V_{oxy}$ (t) over time in oxyhemoglobin concentration.

Explained next is the measurement method that is used by the light measurement device 1 to obtain measurement data that shows change $\Delta V_{oxy}$ (t) over time in oxyhemoglobin concentration. FIG. 3 is a flowchart that explains one example of a measurement method that is used by the light measurement device 1.

First, in the process performed in step S101, a belt (biomonitor) 60 is worn around the abdomen of the tested subject.

Next, in the process performed in step S102, the biomonitor controller 32 receives biological information W(t) from belt 60 and stores the biological information W(t) in the biological information storage area 54.

Next, in the process performed in step S103, the task period start time determination unit 35 determines whether or not the biological information W(t) has exceeded a reference threshold value ($-W_a \times 0.1$) after once decreasing to a lower threshold value ($-W_a \times 0.9$) (i.e., whether or not the condition has been met). If it is determined that the reference threshold value ($-W_a \times 0.1$) was not exceeded after once decreasing to the lower threshold value ($-W_a \times 0.9$), the process returns to step S102.

On the other hand, if it is determined that the reference threshold value ($-W_a \times 0.1$) was exceeded after once decreasing to the lower threshold value ($-W_a \times 0.9$), the process in step S104 is performed wherein the task period start time determination unit 35 sets the starting time $t_a$ of the task period to be when a set time $\Delta T_2$ (e.g., 100 milliseconds) has elapsed after detecting that the reference threshold value ($-W_a \times 0.1$) was exceeded after once decreasing to the lower threshold value ($-W_a \times 0.9$). Together with this, an image is displayed on monitor screen 23a that instructs to transition to the task period starting time $t_a$.

Next, in the process performed in step S105, the task period start time determination unit 35 determines whether or not a task time Y (e.g., 10 seconds) has elapsed from the starting time $t_a$. If it is determined that task time Y has not yet elapsed, the process of step S105 is repeated.

On the other hand, if it is determined that task time Y has elapsed, the process in step S106 is performed wherein the task period start time determination unit 35 displays an image that instructs that the task period be ended at ending time ($t_a+Y$).

Lastly, in the process performed in step S107, the light measurement device 1 displays on monitor screen 23a the measurement data that shows the change $\Delta V_{oxy}$ (t) in oxyhemoglobin concentration over time. The process indicated by this flowchart ends when the process performed in step S107 is completed.

As afore-described, with the light measurement device 1, measurement data that is reproducible and free of variability and with lessened effects of biological information W(t) caused by respiration and therefore not caused by the task is obtained without the tested subject having to repeatedly perform the task.

Embodiment 2

Figure 15:
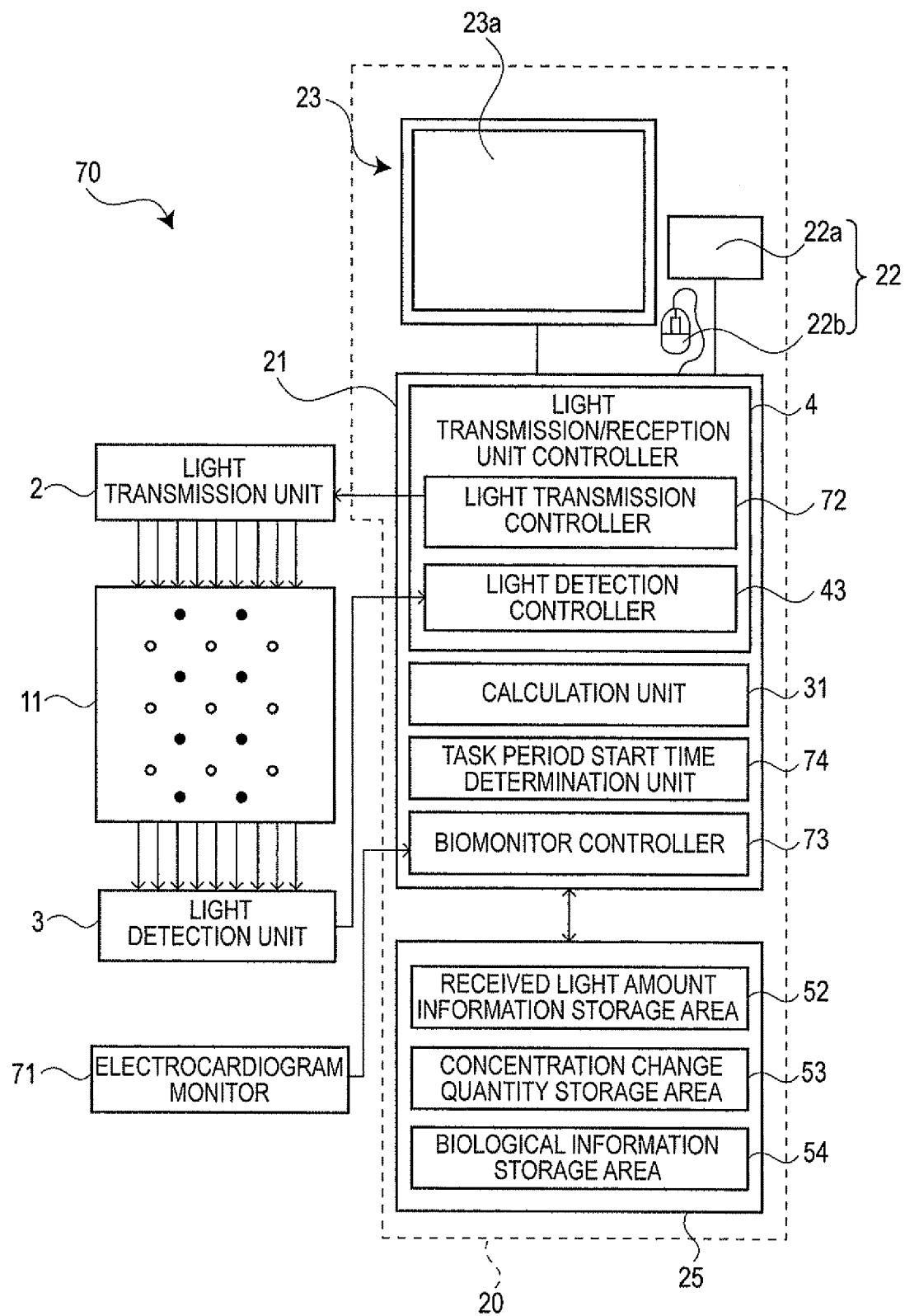
FIG. 15 is a block diagram showing the configuration of one embodiment of a light measurement device according to the present invention.

FIG. 15 is a block diagram showing the configuration of another embodiment of a light measurement device according to the present invention. The light measurement device 70 includes: a light transmission/reception unit 11 that is installed on the surface of the scalp of the tested subject; a light transmission unit 2; a light detection unit 3; an electrocardiogram monitor (biomonitor) 71; and a controller (computer) 20 that controls the overall light measurement device 70.

Unlike the afore-described light measurement device 1, the light measurement device 70 does not determine the starting time $t_a$ of the task period based on biological information W(t) but instead determines the emission starting time $t_{bn}$, when light is emitted to the scalp surface by a first light transmission probe 12. Furthermore, unlike the afore-described light measuring device 1, light measurement device 70 obtains biological information W(t), not from a belt (biomonitor) 60, but from an electrocardiogram monitor (biomonitor).

The same reference numbers are assigned to similar components as in light measurement device 1 and their description is omitted here.

With the light measurement device 70, the "load" that is imposed on the tested subject is to watch a visual stimulus which consists of viewing an image (e.g., flashing grid pattern) for a specific time Y (e.g., 10 seconds).

Physicians, medical technicians and the like observe the change $\Delta V_{oxy}$ (t) over time in oxyhemoglobin concentration as the tested subject is subjected to the visual stimulus during the task period to evaluate the rising edge (slope) of the change $\Delta V_{oxy}$ (t) in oxyhemoglobin concentration which is said to characterize certain mental disorders.

Figure 17A:
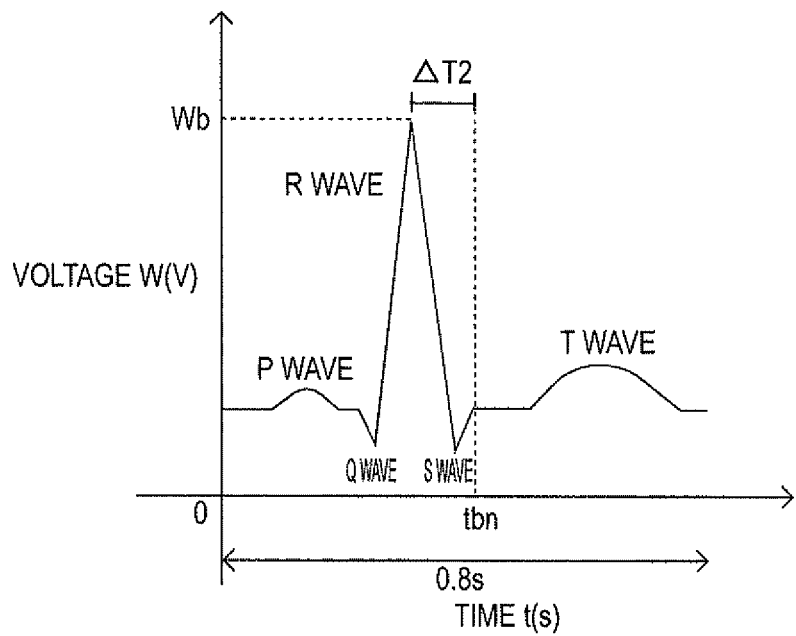
FIG. 17 shows one example of biological information that is detected by an electrocardiogram monitoring device.
Figure 17B:
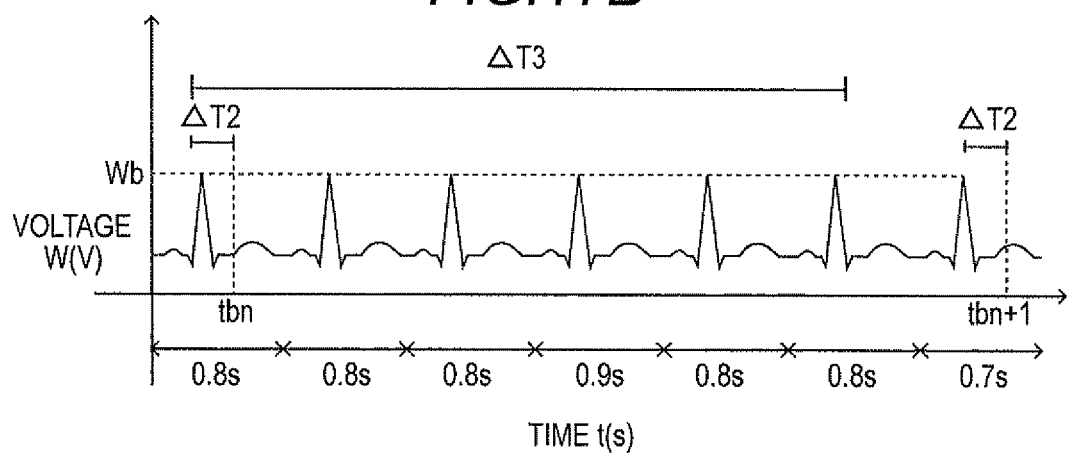

The electrocardiogram monitor (biomonitor) 71 includes electrodes that are attached to the chest, arms and legs of the tested subject to detect biological information W(t) arising from blood pressure. FIG. 17(a) and FIG. 17(b) show examples of biological information W(t) that is detected by the electrocardiogram monitor 71. In the biological information W(t), voltage is plotted along the vertical axis while time t is plotted along the horizontal axis. As FIG. 17(a) shows, the biological information W(t) that appears with each heart beat generally includes five waves: the P wave, Q wave, R wave, S wave and T wave. Among them, the more conspicuous Q wave, R wave and S wave are collectively referred to as the QRS wave. The period of a biological information W(t) such as this is approximately 0.8 seconds. Just like the Mayer Wave, the period of a biological information W(t) such as this varies slightly with the same person and may become, for example, 0.7 seconds or 0.9 seconds. The electrocardiogram monitor 71 outputs the detected biological information W(t) to computer 20.

The processes performed by the CPU 21 can be divided into the following functional blocks: a light transmission/reception unit controller 4 which controls the light transmission unit 2 and the light detection unit 3; a calculation unit 31 which calculates the change $\Delta V_{oxy}$ (t) in oxyhemoglobin concentration; a biomonitor controller 73 which obtains biological information W(t) related to blood pressure; and an emission start time decision unit 74 which determines the emission starting time $t_b$ when a first light transmission probe 12 emits light to the scalp surface.

When the light transmission controller 72 receives a control signal from the emission start time decision unit 74, the light transmission controller 72 controls the output of a drive signal to the light transmission unit 2 that causes light to be sent to the light transmission probe 12. For example, the light transmission controller 72 outputs a drive signal to the light transmission unit 2 that results in light to be sequentially sent to nine light transmission probes 12 in, for example, the following manner: a 780 nm light is first sent to a first light transmission probe 12 for 0.15 seconds, followed by a 805 nm light for 0.15 seconds and then a 830 nm light for 0.15 seconds, which is followed by a 780 nm light to be sent to a second light transmission probe 12 for 0.15 seconds, followed by a 805 nm light for 0.15 seconds and then a 830 nm light for 0.15 seconds. With the light measurement device 70, when the light transmission unit 2 has completed sending light to the ninth light transmission probe 12, the light transmission controller 72 enters a stand-by state wherein it waits for a control signal from the emission start time decision unit 74.

As the biomonitor controller 73 receives biological information W(t) from the electrocardiogram monitor 71 at a set time interval $\Delta T_1$ (e.g., 0.1 seconds), the biomonitor controller 73 performs a control so that the biological information W(t) is stored in the biological information storage area 54.

As shown in FIG. 17(b), the biological information W(t) is caused by, for example, blood pressure will repeat with a period of approximately 0.8 seconds and have a maximum value of the QRS wave of $+W_b$.

Based on the biological information W(t), the emission start time decision unit 74 determines the emission starting time $t_{bn}$ when light is emitted to the scalp surface from a first light transmission probe 12 and also controls the transmission of a control signal to the light transmission controller 72 which instructs the light transmission controller 72 to output a drive signal.

Specifically, the emission start time decision unit 74 detects when the biological information W(t) has exceeded a reference threshold value $W_b$ and determines the first emission starting time $t_{b1}$ to be when a set time $\Delta T_2$ (e.g., 100 milliseconds) has elapsed after detecting that biological information W(t) has exceeded the reference threshold value $W_b$. At the same time, the emission start time decision unit 74 sends a control signal to the light transmission controller 72 that instructs the light transmission controller 72 to output a drive signal that includes an instruction for a first light transmission probe 12 to emit light to the scalp surface at emission starting time $t_{b1}$.

The emission start time decision unit 74 determines the second emission starting time $t_{b2}$ to be when a set time $\Delta T_3$ has elapsed from the starting time $t_{b1}$. For example, $\Delta T_3$ can be the sum of the time (4.05 seconds=0.15 seconds×3 wavelengths×9 probes) required for light to be emitted from nine light transmission probes 12 and a set time $\Delta T_2$ (e.g., 100 milliseconds) that the emission start time decision unit 74 waits to elapse after detecting that the biological information W(t) has exceeded the reference threshold value $W_b$. The emission start time decision unit 74 also sends a control signal to the light transmission controller 72 that instructs the light transmission controller 72 to output a drive signal that includes an instruction to a first light transmission probe 12 to emit light to the scalp surface at emission starting time $t_{b2}$.

This process is repeated as the emission start time decision unit 74 decides the n-the mission starting time $t_{bn}$.

As a result, the light measurement device 70 detects when the biological information W(t) has exceeded the reference threshold value $W_b$ and uses the elapse of a set time $\Delta T_2$ (e.g., 100 milliseconds) after the above detection to determine the emission starting time $t_{bn}$, thus providing measurement data that is reproducible, free of variability and with lessened effects of biological information W(t) caused by blood pressure.

When observing the measurement data that is obtained by the light measurement device 70, physicians, medical technicians and the like observe and evaluate the rising pattern of the change $\Delta V_{oxy}$(t) in oxyhemoglobin concentration, aware in advance that biological information W(t) having a certain waveform caused by blood pressure is superimposed on the observed change $\Delta V_{oxy}$(t) in oxyhemoglobin concentration. The blood pressure causes change $\Delta V_{oxy}$(t) over time in oxyhemoglobin concentration of a certain waveform.

Figure 16:
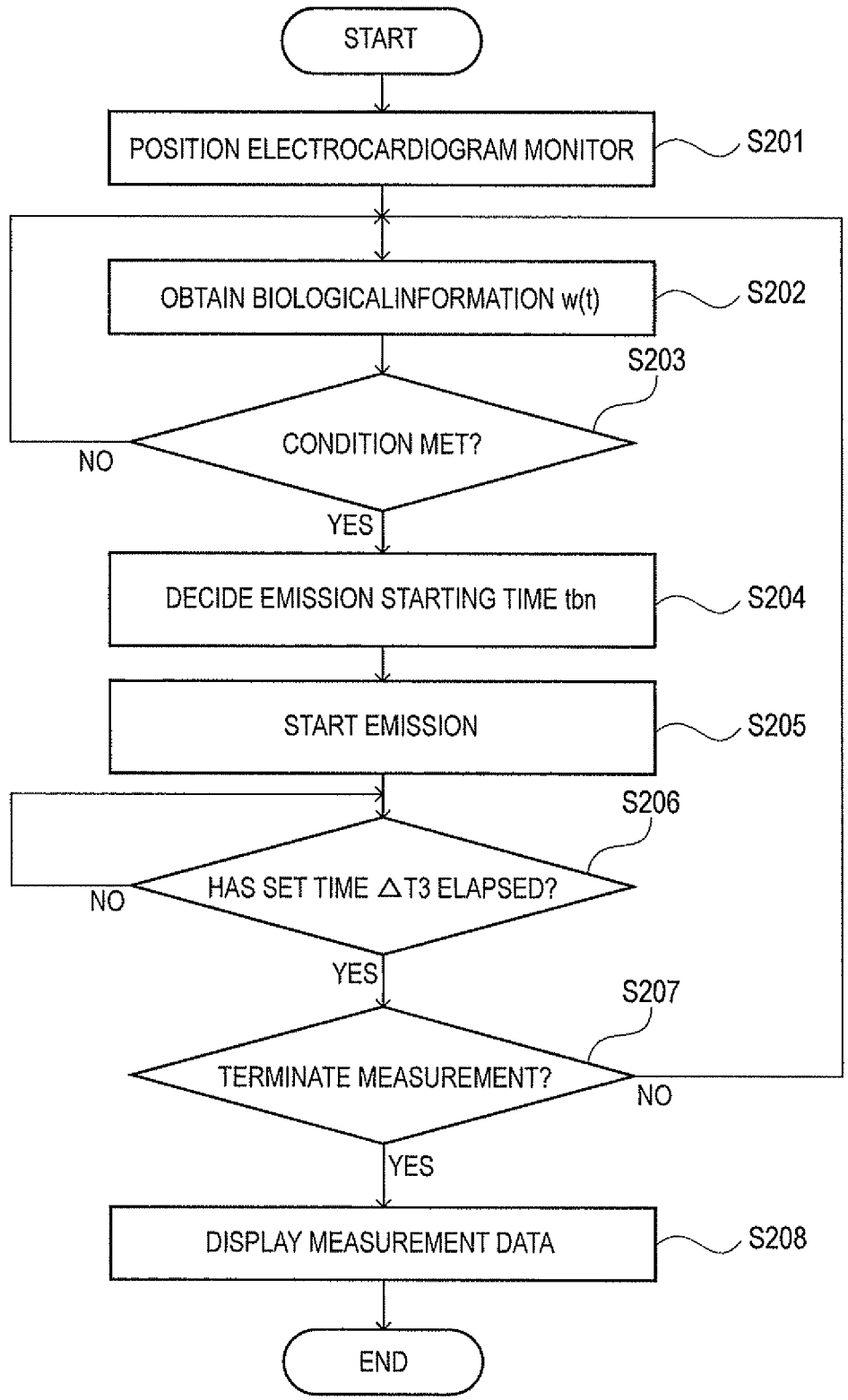
FIG. 16 is a flowchart used for explaining another example of a measurement method performed by the light measurement device.

Explained next is the measurement method that is used by the light measurement device 70 to obtain measurement data that shows the change $\Delta V_{oxy}$(t) over time in oxyhemoglobin concentration. FIG. 16 is a flowchart that explains one example of a measurement method that is used by the light measurement device 70.

First, in the process performed in step S201, an electrocardiogram monitor (biomonitor) 71 is attached to the tested subject.

Next, in the process performed in step S202, the biomonitor controller 73 receives biological information W(t) from electrocardiogram monitor 71 and stores the biological information W(t) in biological information storage area 54.

Next, in the process performed in step S203, the emission start time decision unit 74 determines whether or not the biological information W(t) has exceeded a reference threshold value $W_b$ (whether or not the condition has been met). If it is determined that the reference threshold value $W_b$ was not exceeded, the process returns to step S202.

On the other hand, if it is determined that the reference threshold value $W_b$ has been exceeded, the emission start time decision unit 74 determines in the process performed in step S204 that the emission starting time $t_{bn}$ is when a set time $\Delta T_2$ (e.g., 100 milliseconds) has elapsed after detecting that biological information W(t) has exceeded a reference threshold value $W_b$. At the same time, the emission start time decision unit 74 sends a control signal to the light transmission controller 72 that instructs the light transmission controller 72 to output a drive signal at emission starting time $t_{bn}$ to the first light transmission probe 12 to emit light to the scalp surface Next, in the process performed in step S205, the light transmission controller 72 and the light detection controller 43 output a drive signal to the light transmission unit 2 and also receive received light amount information $\Delta A_{780}$ (t), $\Delta A_{805}$ (t) and $\Delta A_{830}$ (t) from light detection unit 3 and store the received light amount information $\Delta A_{780}$ (t), $\Delta A_{805}$ (t) and $\Delta A_{830}$ (t) in the received light amount information storage area 52.

Next, in the process performed in step S206, the emission start time decision unit 74 determines whether or not a set time $\Delta T_3$ has elapsed from starting time $t_{bn}$. If it is determined that the set time $\Delta T_3$ has not elapsed from the starting time $t_{bn}$, the process of step S206 is repeated.

On the other hand, if it is determined that the set time $\Delta T_3$ has elapsed from the starting time $t_{bn}$, a determination is made in the process performed in step S207 as to whether or not to terminate the measurements. If a decision is made not to terminate the measurements, the process returns to step S202. In other words, until a decision is made to terminate the measurements, whenever the light transmission controller 72 receives a control signal from the emission start time decision unit 74, the light transmission controller 72 outputs a drive signal that instructs the light transmission probe 12 to emit light to the scalp surface at emission starting time $t_{bn}$.

On the other hand, if a decision is made to terminate the measurements, the light measurement device 70 displays on the monitor screen 23a, in the process performed in step S208, the measurement data that shows the change $\Delta V_{oxy}$(t) over time in oxyhemoglobin concentration.

The process identified by the flowchart is terminated when the process of step S208 is completed.

As afore-described, with the light measurement device 70, measurement data that is reproducible and free of variability and with lessened effects of biological information W(t) caused by blood pressure and therefore not caused by the task is obtained without the tested subject having to repeatedly perform the task.

Furthermore, since reproducible measurement data free of variability is obtained, if a brain-machine interface is used to control some apparatus when the change $\Delta V_{oxy}(t)$ in oxyhemoglobin concentration exceeds a certain peak value (threshold value), the apparatus can be controlled with precision.

Other Embodiments (1) With the afore-described light measurement device 1, the light transmission/reception unit 11 had nine light transmission probes 12 and eight light reception probes 13, but the light transmission/reception unit may have a different number of probes such as twelve light transmission probes and twelve light reception probes.

(2) With the afore-described light measurement device 1, a belt (biomonitor) 60 was used to obtain biological information W(t) related to respiration, but the device can be configured so that biological information W(t) related to heart rate is obtained by accelerometers that are attached to the tested subject.

Industrial Use

The present invention can be used to measure change over time in blood flow or in oxygen supply to various intracerebral parts and as oxygen monitor and the like for diagnosing whether a biological tissue is normal or not.

DESCRIPTION OF THE NUMERICAL REFERENCES

1, 70. Light measurement device
4. Light transmission/reception unit controller
11. Light transmission/reception unit
12. Light transmission probe
13. Light reception probe
22. Input device
23. Display device
25. Memory (storage unit)
31. Calculation unit
32, 73. Biomonitor controller
35. Task period start time determination unit
60. Belt (biomonitor)
74. Emission start time decision unit

What is claimed is:

1. A light measurement device for obtaining measurement data that shows change over time in hemoglobin concentration while a subject is performing a load during a task period, said light measurement device comprising:
   a light transmission/reception unit comprising light transmission probes arranged to be positioned on the surface of a scalp of said subject and light reception probes arranged to be positioned on the surface of said scalp;
   a light transmission/reception unit controller for obtaining received light amount information regarding measurement sites of a brain of said subject by controlling so that said light transmission probes emit light to the scalp surface and said light reception probes detect light that emerges from the scalp surface;
   a calculation unit for calculating the change in hemoglobin concentration based on said received light amount information;
   a biomonitor arranged to be positioned on the skin surface of said subject for detecting biological information related to heart rate, blood pressure or respiration of said subject;
   a biomonitor controller for obtaining biological information from said biomonitor; and
   a task period start time determination unit for determining a starting time for said task period based on said biological information.

2. The light measurement device according to claim 1 wherein said task period start time determination unit displays an image instructing transition to said task period at said task period starting time.

3. The light measurement device according to claim 1 wherein said task period start time determination unit starts imposing a load on said tested subject at said task period starting time.

4. A light measurement device for obtaining measurement data that shows change over time in hemoglobin concentration while a tested subject is performing a load during a task period, said light measurement device comprising:
   a light transmission/reception unit comprising light transmission probes arranged to be positioned on the surface of a scalp of said tested subject and light reception probes arranged to be positioned on the surface of said scalp;
   a light transmission/reception unit controller for obtaining received light amount information regarding measurement sites of a brain of said tested subject by controlling so that said light transmission probes emit light to the scalp surface and said light reception probes detect light that emerges from the scalp surface;
   a calculation unit for calculating the change in hemoglobin concentration based on said received light amount information;
   a biomonitor arranged to be positioned on the skin surface of said tested subject for detecting biological information related to heart rate, blood pressure or respiration of said tested subject;
   a biomonitor controller for obtaining biological information from said biomonitor;
   and
   an emission start time decision unit for determining the emission starting time for emitting light from said light transmission probe to a scalp surface based on said biological information.

5. The light measurement device according to any one of claims 1 through 4 wherein the biomonitor is configured for obtaining biological information related to the respiration of said tested subject and is a respiration monitoring device or an elastic belt that is adapted to be worn around the abdomen or chest of said tested subject.

6. The light measurement device according to any one of claims 1 through 4 wherein the biomonitor is configured for obtaining biological information related to the blood pressure of said tested subject and is a pressure sensor device that is adapted to be attached to said tested subject or an electrocardiogram monitor wherein electrodes are adapted to be attached to the chest or arms and legs of said tested subject.

7. The light measurement device according to any one of claims 1 through 4 wherein the biomonitor is configured for obtaining biological information related to the heart rate of said tested subject and is an accelerometer that is adapted to be attached to said tested subject.

* * * * *